United States Patent
Meilke

(12) 
(10) Patent No.: US 6,485,757 B1
(45) Date of Patent: Nov. 26, 2002

(54) METHOD OF PRODUCING A LIQUID ENRICHED WITH PLANT SUBSTANCES, LIQUID FORMED THEREBY, AND PRODUCTS FORMED THEREFROM

(76) Inventor: Gerd Rudolf Meilke, Thomas-Müntzer Strasse 12, D-06242 Krumpa (DE)

( * ) Notice: Subject to any disclaimer, the term of this patent is extended or adjusted under 35 U.S.C. 154(b) by 0 days.

(21) Appl. No.: 09/601,889
(22) PCT Filed: Feb. 23, 1999
(86) PCT No.: PCT/DE99/00490
§ 371 (c)(1), (2), (4) Date: Feb. 26, 2001
(87) PCT Pub. No.: WO99/42114
PCT Pub. Date: Aug. 26, 1999

(30) Foreign Application Priority Data

Feb. 24, 1998 (DE) .......................................... 198 07 731

(51) Int. Cl.⁷ ................................................ A61K 35/78
(52) U.S. Cl. ........................ 424/725; 424/400; 424/464
(58) Field of Search ................................ 424/400, 401, 424/464, 451 T, 486, 489, 725 T, 195.17, 451

(56) References Cited

U.S. PATENT DOCUMENTS 5,676,957 A * 10/1997 Nakamura et al.

FOREIGN PATENT DOCUMENTS

DE 197 11 809 A1 9/1998

OTHER PUBLICATIONS

English language abstract of Japanese patent publication No. 4–262947.

* cited by examiner

Primary Examiner—Leon B. Lankford, Jr.
Assistant Examiner—Ruth Davis
(74) Attorney, Agent, or Firm—Staas & Halsey LLP

(57) ABSTRACT

Described is a method of producing a liquid enriched with ingredients and active agents of plants using a carrier and storage material for plants and their active agents, as well as the use of the liquids. It is characteristic of the invention that used-type material is mixed with the entire plant, the carrier material takes-up the same, and the resulting mixture is dried, compressed or dried in moulds so that it may be stored for a long period of time without losses of active agent occurring or the material deteriorating; for use of the material as a cosmetic agent, or its application in therapy, leisure activities, household and sports, it is sufficient to mix the carrier material with a liquid in a defined mixing ratio, at a suitable temperature, and for a certain period of time, depending on the intended application.

14 Claims, No Drawings

METHOD OF PRODUCING A LIQUID ENRICHED WITH PLANT SUBSTANCES, LIQUID FORMED THEREBY, AND PRODUCTS FORMED THEREFROM

The invention relates to a method of producing a liquid enriched with ingredients and active agents of plants using a carrier and storage material for plants and their ingredients.

Methods of producing plant extracts are known, in which it is attempted to obtain the active agents and ingredients by squeezing or centrifuging the plants, preparing a mixture thereof in alcohol, and storing them in liquid form. Known is also the method for drying plants, as used with medicinal herbs and tea. These methods have the disadvantage that only a part of the active substances is bound.

Chemical methods are also known, in Which the active substances are obtained chemically. In these, however, only the desired principal active agent is produced at any time; a mixture such as that occurring in nature is not possible or involves too much outlay.

Moreover, methods are known for producing plant extracts by steam extraction. Thus, for example, 15 liters of tea tree oil are obtained from 6 tons of tea tree leaves. The disadvantages of this method are a very large expenditure of energy for steam generation and a high proportion of residual waste material.

Known is also a filter and carrier material according to the patent application Ser. No. 197 11 809.7. In this, provision is made for the use of the carrier material as a store for medicinal and other therapeutic agents and their use in a gaseous state in suitable and conventional apparatus. A production of liquids from the carrier material was not envisaged. Moreover, it is not known to bind material from plants completely in a filter or carrier material.

It is the object of the invention to develop a low-cost method for producing a liquid enriched with ingredients and active agents of plants, which makes it possible to bind the plants and their active agents in a comminuted form, to store them for a long period of time, and to release them during a mixing with liquids in such manner that their use as a medicinal, cosmetic, therapeutic agent for sports and leisure applications, and also their use as a cleaning agent in households and industry becomes possible.

If used as a glass cleaning agent, the product is intended to produce an anti-glare effect on car windscreens at night. When used for medical or therapeutic applications, the preparations is intended to produce an efficiency better than that of preparations produced by conventional means, because it is successfully possible 1. to preserve the naturally occurring mixture of active substances,
2. to release a high percentage of the active substances to the liquid again, with the carrier material acting simultaneously as both a preserving agent and a catalyst increasing the efficiency of the liquid.

In accordance with the present invention the problem is solved by the provisions that the plants are comminuted by means of cutting tools in such a way that a spinach-like mass is created. Depending on the species of the plants, this mass is mixed with a specific amount of rubber granules either in a pure form or with a mixture of rubber granules and textile components adhering thereto, as this is described in accordance with PA AZ 196 48 551.7 of Jun. 12, 1997, until it can be shaped. Then the resulting mass is dried either mechanically or in air. The resulting carrier material is able to store up to 97 per cent of all the ingredients of the plants, with the possibility to detect a level of 11 to 24 per cent of easily volatile ingredients and the balance of ingredients at a level between 65 and 97 per cent. For an application as intended the carrier material enriched with plants is mixed with a liquid at a specific mixing ratio at a defined temperature for a defined period of time, which is different as a function of the purpose.

The solution so obtained is stable over a long time and is used for different applications in medicine, cosmetics, as therapeutic agent in sports and leisure activities, or as detergent for household, industrial and trade purposes.

Embodiments

1. Stinging nettle plants are comminuted by means of cutting tools until a spinach-like paste is produced. This paste is mixed with rubber granules either in a pure form or with rubber granules mixed with textile components (PA AZ 196 48 551.7 of Jun. 12, 1997) until a mouldable mass is created. The resulting mass is shaped expediently, e.g. in the form of tablets having a diameter of 3 cm approximately, and dried. Prior to the intended application, the tablets are prepared with a liquid, preferably water, and allowed to stand over a defined period of time at a specific temperature.

Then the liquid is drawn off and bottled.

1.1. This liquid is used as glass cleaning agent for car windows, exterior and interior car mirrors as well as for head-lights. To this end, the liquid is sprayed on the pre-cleaned car windows (both outside and inside), the mirrors and the headlight panes, and is polished dry. This surface treatment produces the effect that highly polished panes with an improved depth of focus are achieved. The glaring effect of oncoming vehicles at night is substantially reduced. Even with a slight soiling of the panes this effect is noticeable.

After normal cleaning, the effect is present again like after the first treatment. The treatment of the panes and the mirrors results in a distinct reduction of the glaring effect of oncoming vehicles or of vehicles approaching too closely. The treatment of the headlight glass allows for a higher yield of light.

1.2. The liquid produced in accordance with Example 1 is applied on spectacle glasses, magnifying glasses or lenses. The glasses are then polished dry. Clean and shining surfaces are produced. The anti-glare effect equally occurs at night.

1.3. The same liquid is sprayed on window panes and is equally polished dry. In addition to the properties so far described, the panes become dirt-repellent, and dirt can be removed again more easily. Subsequent window cleaning can be done with clear water alone over a major period of time before the panes are primed again with the liquid according to Example 1.

Identical positive effects of the liquid, when used as detergent and preserving agent, were achieved in the treatment of tiles, chrome-plated parts such as taps, towel-holders and clothes dryers, etc.

1.4. Some liquid according to Example 1 was used as refreshing and cleansing tonic by application thereof by rubbing into the skin or spraying. The effects are an improved feeling of well-being, cooling and pore-deep cleaning, as well as a subsequent formation of a protective layer.

1.5. The liquid according to Example 1 was very well suitable for use in the fields of sports and leisure activities. It is a remedy in cases of myogelosis, contusions, muscular soreness, strain and overstretching, etc. It is used, for instance, as a spray, as liniment or for massages, or as a bath essence or infusion substance in the sauna.

1.6. The liquid according to Example 1 was suitable as hair restorer and hair care preparation in known applications such as washing or rubbing-in or spraying.

1.7. The liquid according to Example 1 was successfully used within the scope of oxygen therapy by adding it as a fine mist to the oxygen at the spraying nozzle.

1.8. Some liquid according to Example 1 is applied on synthetic surfaces and subsequently polished. By doing so, dirt and stains, insects and their excrement or nicotine deposits are carefully removed. Equal good results were achieved with application on Ceran range tops.

2. Some liquid produced in accordance with Example 1 were mixed with further vegetable substances and/or algae in a liquid or dry form. Therapeutic and cosmetic products can be produced from this mixture. The mixture is also suitable as an active substance and additive for creams, liniments or sprays such as those used in cosmetics or in medical treatments.

2. Medicinal plants or plant mixtures are comminuted by means of cutting tools until a spinach-like paste is produced. This paste is mixed with rubber granules either in a pure form or with rubber granules mixed with textile components (PA AZ 196 48 551.7 of Jun. 12, 1997) until a mouldable mass is produced. The resulting mass is expediently shaped, e. g. in the form of tablets having a diameter of roughly 3 cm, and dried. Prior to the intended application, the tablets are prepared with a liquid, preferably water, and allowed to stand over a defined period of time at a specific temperature. Then the resulting liquid is drawn off and bottled. The product is equally applied by rubbing in, spraying, in a bath, etc.

3. Algae in a dry or liquid form are mixed with comminuted stinging nettle plants or liquids according to Example 1 and rubber granules either in a pure form or in the form of granules mixed with textile components (PA AZ 196 48 551.1) until a mouldable paste is formed. The resulting mass, in an appropriately moulded and dried condition, is capable of storing the components of the mixture over a long period of time. The dried mass is prepared for the intended application in the same manner as that described in Examples 1 and 2.

What is claimed is:

1. A method of producing a liquid enriched with plant substances, comprising:

comminuting plants, or a mixture of plants and algae with cutting tools to form a paste;

mixing the paste with a pure rubber granulate or a rubber granulate with a textile adhered thereto, until it can be molded;

after mixing, molding the paste into a molded mass;

drying the molded mass to form a bound-together dried mass;

storing the bound-together dried mass without deterioration;

mixing the bound-together dried mass with a liquid; and separating the liquid enriched with plant substances from remaining solids.

2. A method of producing a liquid enriched with plant substances according to claim 1 wherein the liquid enriched with plant substances according to claim 1 is mixed with:

more plants, or a mixture of plants and algae.

3. A method for producing a liquid enriched with plant substances according to claim 2, wherein the step of comminuting plants, or a mixture of plants and algae involves comminuting stinging nettles.

4. A method for producing a liquid enriched with plant substances according to claim 2, wherein the step of comminuting plants, or a mixture of plants and algae involves comminuting at least stinging nettles and medicinal herbs.

5. A method for producing a liquid enriched with plant substances according to claim 2, wherein the step of comminuting plants, or mixtures of plants and algae involves comminuting plants and algae.

6. A method for producing a liquid enriched with plant substances according to claim 5, wherein the algae is dried algae.

7. A method for producing a liquid enriched with plant substances according to claim 5, wherein the algae is liquid algae.

8. A method for producing a liquid enriched with plant substances according to claim 2, wherein the molded mass is a tablet.

9. A method for producing a liquid enriched with plant substances according to claim 1, wherein the step of comminuting plants, or a mixture of plants and algae involves comminuting stinging nettles.

10. A method for producing a liquid enriched with plant substances according to claim 1, wherein the step of comminuting plants, or a mixture of plants and algae involves comminuting at least stinging nettles and medicinal herbs.

11. A method for producing a liquid enriched with plant substances according to claim 1, wherein the step of comminuting plants, or mixtures of plants and algae involves comminuting a mixture of plants and algae.

12. A method for producing a liquid enriched with plant substances according to claim 11, wherein the algae is dried algae.

13. A method for producing a liquid enriched with plant substances according to claim 11, wherein the algae is liquid algae.

14. A method for producing a liquid enriched with plant substances according to claim 1, wherein the molded mass is a tablet.

* * * * *